United States Patent [19]

Derenzo et al.

[11] Patent Number: 5,015,861
[45] Date of Patent: May 14, 1991

[54] LEAD CARBONATE SCINTILLATOR MATERIALS

[75] Inventors: Stephen E. Derenzo, Pinole; William W. Moses, Berkeley, both of Calif.

[73] Assignee: Regents of the University of California, Oakland, Calif.

[21] Appl. No.: 383,158

[22] Filed: Jul. 20, 1989

[51] Int. Cl.$^5$ .................. G01T 1/202; G01T 1/164
[52] U.S. Cl. .................. 250/361 R; 250/363.03; 252/301.18
[58] Field of Search .................. 252/301.17, 301.18; 250/361 R, 363.03, 366, 367

[56] References Cited

U.S. PATENT DOCUMENTS 3,244,637  4/1966  Tsou et al. .................. 252/301.18

OTHER PUBLICATIONS

Moon, "Inorganic Crystals for the Detection of High Energy Particles and Quanta", Phys. Rev. 73 (10), May, 1948, p. 1210.

*Primary Examiner*—Carolyn E. Fields
*Attorney, Agent, or Firm*—Robert W. Mulcahy; Robert J. Henry; Berthold J. Weis

[57] ABSTRACT

Improved radiation detectors containing lead carbonate or basic lead carbonate as the scintillator element are disclosed. Both of these scintillators have been found to provide a balance of good stopping power, high light yield and short decay constant that is superior to other known scintillator materials. The radiation detectors disclosed are favorably suited for use in general purpose detection and in medical uses.

9 Claims, 2 Drawing Sheets

LEAD CARBONATE SCINTILLATOR MATERIALS

This invention was made with U.S. Government funding support under prime Contract No. DE-AC03-76SF00098, awarded by the United States Department of Energy. The U.S. Government has certain rights in the invention.

FIELD OF THE INVENTION

Scintillators are materials that emit flashes or pulses of light when they interact with ionizing radiation such as gamma rays. The present invention relates to radiation detection devices utilizing an improved scintillating material. More particularly, the present invention relates to the use of lead carbonate ($PbCO_3$) as the scintillating component both in general purpose radiation detectors and in the specific application of positron emission tomography (PET).

BACKGROUND OF THE INVENTION

High energy ionizing radiation such as a gamma ray cannot be detected directly; it must be converted into an electrical pulse. One common method for creating an electrical pulse when ionizing radiation is present is to first absorb the ionizing radiation in a scintillator. In response, the scintillator then produces a flash of light which is converted into an electrical signal by a photodetector.

Although the physical configuration of the scintillator/photodetector combination varies from application to application, the underlying principle remains constant. The scintillator will vary in size, but must be thick enough to stop the incident radiation and large enough to cover the desired area. The exact type of photodetector that the scintillator is coupled to varies but the photodetector must produce an electrical signal large enough to be observable above background noise.

The effectiveness of this method of radiation detection is primarily limited by the scintillating material. Only a few materials are known to scintillate, and the scintillation properties of these materials vary. An ideal scintillator would have a high density, a short decay time constant (i.e. the photons are emitted as soon as possible after the radiation interacts in the scintillator), and a large light output that is essentially proportional to the amount of radiation deposited in the scintillator. High density is desirable in order to stop the ionizing radiation in as short a distance as possible, a short decay time is desirable in order to measure the time of interaction accurately, and a high light output is desirable in order to make it easier for the photodetector to convert the light into an electrical pulse. In addition, the scintillating material should not have unpleasant chemical or material properties, such as toxicity, hygroscopy, or extreme reactivity.

The photodetector that converts the scintillation light into an electrical pulse is usually either a photomultiplier tube or a solid-state (Si, GaAs, HgI, etc.) photodiode. A photomultiplier tube (PMT) is usually employed when very small amounts of radiation are to be detected, as a PMT typically converts each photon into approximately 1 million electrons. Photodiodes are usually used when large amounts of radiation are to be detected, as a photodiode typically converts each photon into a single electron. These photodetectors can either be coupled to the scintillator either singly or in position sensitive arrays.

FIG. 1 diagrammatically demonstrates a single embodiment of a high energy radiation detector contemplated in the present invention. The device 10 is in the form of a hand held radiation monitor and is similar to a standard Geiger counter, but will be more sensitive to gamma radiation. A scintillator crystal 11 is optically coupled to a photomultiplier tube 12 and this assembly is encased in an opaque material 13 in order to shield ambient light. A cable 14 connects the scintillator/photodetector assembly to a small box 15 containing a battery operated power supply for the photomultiplier tube, counting electronics, and a numerical display. When ionizing radiation 17 from a source 16 impinges on the scintillator crystal, it emits photons which are converted into an electrical pulse by the photomultiplier tube 12 and the rate at which these pulses arrive is determined by the electronic circuit in the box 15 and displayed accordingly. As this rate is proportional to the amount of radiation present, the device can be used to monitor radiation.

A more complicated embodiment of a radiation detector is a radioisotope camera. Radioisotope cameras have considerable important uses in medical diagnosis and research. They have a significant advantage over the use of X-ray techniques in that they are sensitive to minute amounts of certain radioactive tracer compounds. In use, a small quantity of a gamma-ray emitting radioactive substance is injected into a patient. The choice of radioactive isotope depends on its half-life, activity, dose rate, and many other factors. Certain isotopes are highly specific, and tend to concentrate in certain organs of the body. This selective accumulation permits visualization of the biological function of almost every organ of the human body. Although the resolution of radioisotope cameras is not equal to that obtained in X-ray radiographs, the size, shape, position and function of the organs can be determined, and often lesions can be located in them.

PET is a medical imaging technique in which a radioactively labeled substance is administered to a patient and then traced within the patient's body by means of an instrument that detects the decay of the isotope. In the positron emission tomographic process a chemical tracer compound having a desired biological activity or affinity for a particular organ is labeled with a radioactive isotope that decays by emitting a positron (positive electron). The emitted positron loses most of its kinetic energy after traveling only a few millimeters in living tissue. It is then highly susceptible to interaction with an electron, an event that annihilates both particles. The mass of the two particles is converted into 1.02 million electron volts (1.02 MeV) of energy, divided equally between two 511 keV photons (gamma rays). The two photons are emitted simultaneously and travel in opposite directions. The two photons penetrate the surrounding tissue, exit the patient's body, and are absorbed and recorded by radiation detectors geometrically arranged to record the simultaneous emission event.

The instrumentation used in PET is a camera generally in a geometric arrangement consisting of an array of hundreds of scintillation elements in a ring surrounding a radioactive emitting subject. Assuming no scattering, the simultaneously emitted gamma-rays strike two scintillation elements perpendicularly disposed 180 degrees from each other in the scintillation ring array. The scintillation flashes will be detected by photodetectors coupled to the scintillators. Row and column amplifiers and a position logic circuit connected to the scintillator array will then distinguish the electrical pulse generated by the activated scintillation elements. A state of the art PET camera is demonstrated in U.S. Pat. No. 4,672,207 to DERENZO. This patent discloses a radioisotope camera in which an array of scintillation crystals optically coupled to photodetectors arranged in rows and columns and adapted to be exposed to a radioactive emitting subject. The array is further coupled to means for reconstructing the image created by the radioactive emissions from the subject.

Biological activity within an organ under investigation can be assessed by tracing the source of the radiation emitted from the patient's body to the scintillators of the PET camera. The source of the radiation can be accurately estimated by linking each scintillator crystal element with several other scintillators on the opposite side of the array and registering a signal only if two detectors sense 511 keV photons coincidentally (typically 10 nsec). When a coincidence is registered, an annihilation is recorded along a line connecting the two scintillators. In this manner, a circumferential array of photodetectors can establish the sources of all coincident pairs of photons that originate within a volume defined by straight lines joining paired detectors. A computer program reconstructs the spatial distribution of the decaying isotopes within the patient. With suitable interpretation, PET images provide a noninvasive, regional assessment of many biochemical processes associated with human organs.

The value of PET as a clinical imaging technique is in large measure dependent upon the performance of the radiation detection elements. The typical PET camera comprises an array of radiation detectors consisting of scintillator crystals coupled to photomultiplier tubes (PMT's). When a photon strikes a detector, it produces light in one of the scintillator crystals that is then sensed by the PMT, which registers the event by passing an electronic signal to the reconstruction processing circuitry.

As pointed out earlier, the scintillator crystals used in a general purpose detector or a PET camera must have certain properties, among which are (1) good stopping power, (2) high light yield, and (3) fast decay time.

In a PET application, stopping power is the ability to stop the 511 keV photons in as little material as possible so as to reduce the overall size of the scintillator, which reduces the cost and improves spatial accuracy. Stopping power is typically expressed as the linear attenuation coefficient (tau) having units of inverse cm$^{-1}$. After a photon beam has traveled a distance "x" in a crystal, the fraction of photons that have not been stopped by the crystal is calculated as follows:

$$\text{fraction of unstopped photons} = e^{(-tau \cdot x)}.$$

Therefore, after traveling a distance of 1/tau (the "absorption length"), approximately 37% of the photons will not have been stopped: 63% will have been stopped. Likewise, 63% of the remaining photons will have been stopped after traveling an additional distance of 1/tau. For PET, one wants 1/tau to be as small as possible so that the photodetector is as compact as possible.

Light yield is also an important property of scintillators contemplated for use in PET. Light yield is sometimes referred to as light output or relative scintillation output, and is typically expressed as the percentage of light output from a crystal exposed to 'standard' scintillation 511 keV photons relative to the light output from a crystal, thallium-doped sodium iodide, NaI(Tl) under the same conditions. Accordingly, the light yield for NaI(Tl) is defined as 100.

A third important property of scintillators in PET applications is decay time. Scintillation decay time, sometimes referred to as the time constant or decay constant, is a measure of the duration of the light pulse emitted by a scintillator, and is typically expressed in units of nanoseconds (nsec). As noted above, in PET, the source of biological activity within an organ under investigation is determined by tracing the source of coincident photons emitted from the patient's body to the photodetectors. When two 511 keV photons are detected at the same time by a pair of scintillators, the source of the photons is known to lie along the linear path connecting the two scintillators. In general, only a fraction of the detected photons are in coincidence and thus used in the reconstruction analysis. Moreover, many false coincidences are registered because the finite decay time associated with each scintillator may cause it to emit light at the same time as another scintillator when in fact the photons inducing the light did not come from the same positron annihilation. For example, a photon arrived at one photodetector may produce a flash of light that does not decay, i.e. "turn off", until after a later photon, from a different positron annihilation, produces a flash of light in a detector on the side opposite the first detector. In this instance, the flashes would overlap, and the photodetectors would register them as in coincidence. Thus, scintillator materials with long decay constants have an inherent problem in detecting coincident photons.

In addition to the problem of false coincidences, the positron emitting tracer compounds themselves typically have very short half-lives. In fact, most medical facilities performing PET also operate on-site accelerators to produce the short-lived radioactively labeled tracer compounds. Because of the short half-lives of these compounds, data on the occurrence of coincident photons needs to be gathered at as high a rate as possible. As noted above, the majority of the detected photons are not in coincidence, i.e., they are from sources outside the plane of the detector array. Consequently, if a scintillator's decay constant is short, then more of its time will be available for the detection of coincident photons.

In addition to the three important properties discussed above, scintillator crystals for PET should be easy to handle. For example, certain known scintillators are very hygroscopic, i.e., they react with moisture, making it necessary to very tightly encapsulate them to allow their use as scintillators in PET. These hygroscopic scintillators are expensive and difficult to use.

Known scintillator materials include (1) plastic scintillators, (2) thallium-doped sodium iodide (NaI(Tl)), (3) cesium fluoride (CsF), (4) bismuth germanate ($Bi_4Ge_3O_{12}$, also referred to as "BGO"), (5) cerium fluoride ($CeF_3$), and (6) barium fluoride ($BaF_2$). Of these five scintillators, only two, BGO and $BaF_2$, are used routinely for PET.

Plastic scintillators, typically composed of polystyrene doped with a wavelength-shifting additive, are commercially available under such tradenames as PILOT U and NE 111. Upon excitation with a 511 keV photon, plastic scintillators emit a light pulse having a very fast decay constant of approximately 1.5 nsec and light output proportional to the energy of the incident photon. The main disadvantage of plastic scintillators is their low density (approximately 1.1 to 1.2 g/cm$^3$) due to the light atoms (hydrogen and carbon) that make up the molecules of the material. Because of their low density, plastic scintillators have poor stopping power, and are therefore poorly suited for use in PET.

NaI(Tl), thallium-doped sodium iodide, has the highest light output of the six scintillators listed above. NaI(Tl) also has an intermediate stopping power (1/tau=3.0 cm at 511 keV). However, NaI(Tl) has a long decay constant (250 nsec), a significant disadvantage for use in PET. NaI(Tl) has an additional disadvantage in that it is highly hygroscopic, making it extremely difficult to handle in that it must be tightly encapsulated in bulky cans.

CsF, cesium fluoride, has an advantage over plastic scintillators because of its relatively high density (4.61 g/cm$^3$) and consequent stopping power. However, the light output and decay constant of CsF are inferior to those of plastic scintillators. CsF is also highly hygroscopic, well above NaI(Tl) which, as noted above, makes it expensive and difficult to handle.

BGO has the highest density (7.13 g/cm) of the five known scintillator materials noted above. Its stopping power is the best of the five materials (1/tau=1.1 cm at 511 keV). As a result, BGO is best able to absorb 511 keV photons efficiently in small crystals. However, BGO's very long decay constant (300 nsec), longer even than NaI(Tl), is at a significant disadvantage for use in PET.

Cerium fluoride, CeF$_3$, a recently discovered scintillator, has a relatively high density (6.2 g/cm$^3$) and correspondingly high stopping power. However, its decay time is moderately long (27 ns) and its light output is low.

The use of BaF$_2$ as a scintillator material is described in Allemand et al. U.S. Pat. No. 4,510,394. BaF$_2$ emits light having two components: 75% is emitted with a 'slow' decay constant of approximately 620 nsec and 25% with a 'fast' decay constant of approximately 0.6 nsec. BaF$_2$ has a light yield of approximately 16% that of NaI(Tl) and about half the stopping power of BGO (1/tau=2.3 cm at 511 keV). Unlike CsF and NaI(Tl), BaF$_2$ is not hygroscopic.

The fast component of BaF$_2$ emits light in the ultraviolet region of the spectrum. Glass photomultiplier tubes are not transparent to ultraviolet light, so a quartz photomultiplier tube must be used instead to detect the fast component of BaF$_2$. Since quartz photomultiplier tubes are substantially more expensive than glass, one would prefer to avoid using BaF$_2$, if possible, in favor of using a scintillator that can be detected by a glass photomultiplier tube. The fast component gives BaF$_2$ very good timing resolution, but the slow component limits its high rate capabilities. In other words, it takes longer when using BaF$_2$ to get ready for the next event.

Of the best known scintillator materials, BGO has the best stopping power, NaI(Tl) has the best light yield, and BaF$_2$ has the best timing resolution. However, as noted above, each of these materials have significant shortcomings which hinder their performance as scintillators for PET: BGO has a very long decay constant, NaI(Tl) has a very long decay constant comparatively low density and is hygroscopic, and BaF$_2$ has a long decay constant and requires expensive photomultiplier tubes.

OBJECTS OF THE INVENTION

It is therefore an object of the invention to provide an improved radiation detector having an improved scintillator material.

Another object of the invention is to provide a radiation detector element having enhanced utility for general purpose detection and in PET.

A further object of the invention is to provide a radiation detector containing a scintillator material having a superior balance of stopping power, light yield and decay constant.

SUMMARY OF THE INVENTION

The above objects are accomplished by use of substantially pure lead carbonate (PbCO$_3$) or basic lead carbonate [2(PbCO$_3$)·Pb(OH)$_2$] as a scintillator in radiation detection. Substantially pure lead carbonate and basic lead carbonate both combine a number of ideal scintillator properties, and so their respective use as a scintillator should improve the performance of radiation detection devices. Specifically, each of these inorganic materials has been found to provide a balance of stopping power, light yield and decay constant that is superior to presently known scintillator materials. As a result, substantially pure lead carbonate and basic lead carbonate are each favorably suited for use as a scintillator material for general purpose radiation detectors and in positron emission tomography.

DETAILED DESCRIPTION OF THE PREFERRED EMBODIMENTS

Figure 1:
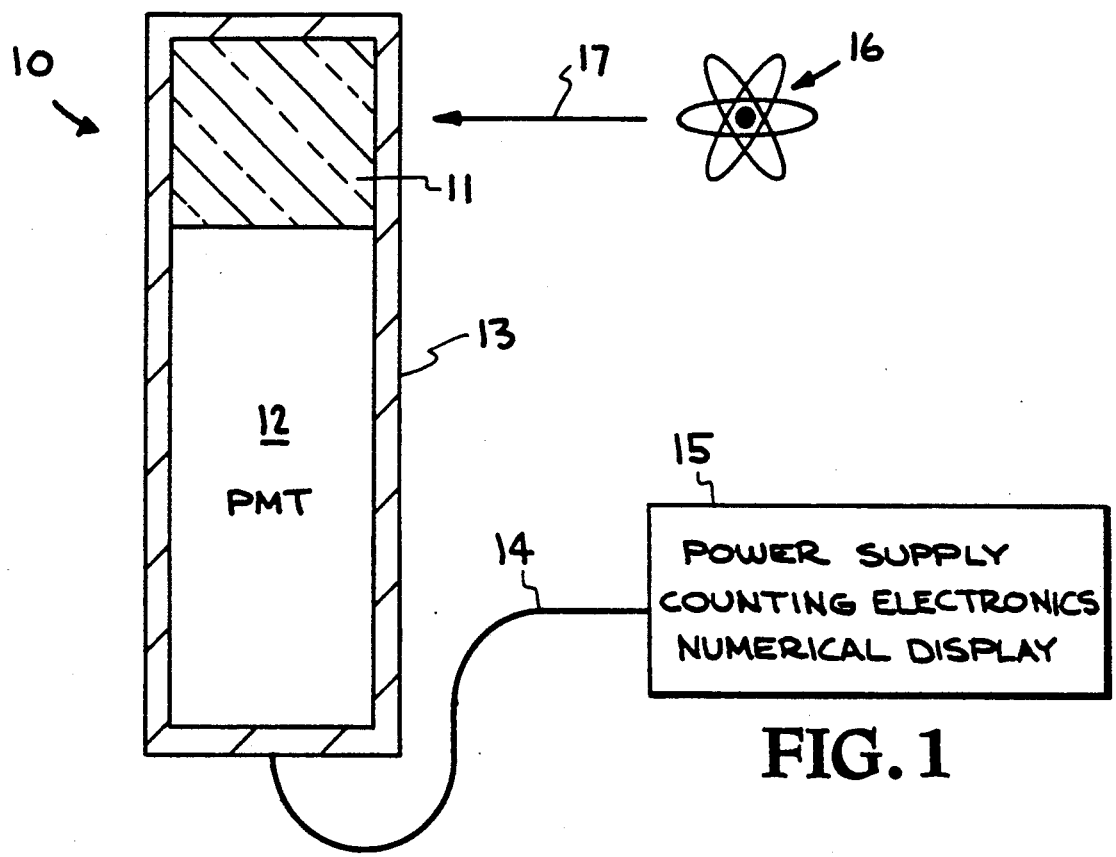
FIG. 1 is a schematic diagram of a general purpose high energy radiation detector device.

As already described above, FIG. 1 schematically illustrates a general purpose radiation detector 10 in which a scintillator crystal element 11 is coupled to photodetector means in the form of a photomultiplier tube 12. The photomultiplier tube 12 is coupled by cable wire 14 to conventional analog electronics assembly 15 which can amplify, discriminate and count incoming signals. A solid-state photodiode can be used instead of photomultiplier tube 12.

Figure 2:
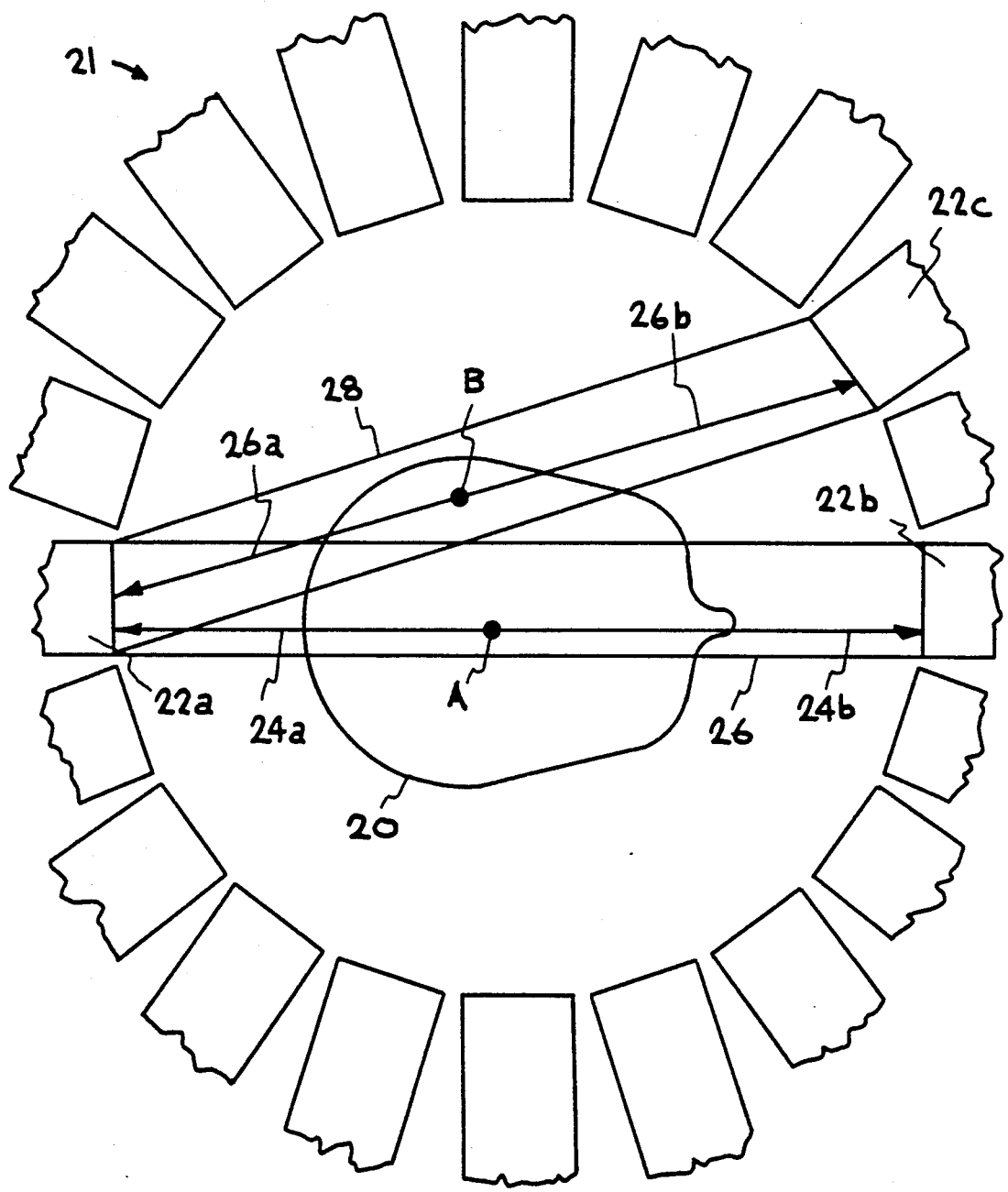
FIG. 2 is a schematic diagram showing the basic mechanism of positron emission tomography in combination with a circular array of detectors.

Turning to FIG. 2 of the drawing, an object 20, such as, for example, a section of a human brain, is shown in cross-section for study using PET. Object 20 is placed between two arrays of oppositely disposed radiation detectors in circular array 21, three of which are illustrated for simplicity in the figure as detectors 22a, 22b and 22c. A radioactively labeled substance having an affinity for object 20 is administered to the patient. The substance decays by emitting a positron (not illustrated), which slows and interacts with electrons (not illustrated) in the tissue of object 20. This positron/electron interaction causes the annihilation of both particles at point A in FIG. 2, producing two 511 keV photons, illustrated as rays 24a and 24b, which are emitted approximately 180 degrees to each other. If rays 24a and 24b are detected simultaneously (in coincidence) by detectors 22a and 22b, then the decay is localized to the space 26 between detectors 22a and 22b.

Positron/electron annihilation occurring elsewhere in the patient such as at point B will be detected by another pair of photodetectors. Thus, if rays 26a in FIG. 2 are detected simultaneously by detectors 22a and 22c, the decay is localized to the space 18 between detectors 22a and 22c. In this manner, the source of photons emitted from within object 20 can be accurately established.

It is to be appreciated that the ring or circular array 21 of detectors 22a, 22b, 22c, etc., are used to localize the source of coincident 511 KeV photons. Detectors 22a, 22b, 22c, etc., are arranged so that only simultaneous events occurring on the opposite side of ring 21 are recorded. For example, an annihilation at point A will produce two 511 keV photons, illustrated as rays 24a and 24b. If rays 24a and 24b are detected simultaneously by the two detectors, 22a and 22b, then the event is recorded. A computer program reconstructs the spatial distribution of the decaying isotopes within the patient by back-projecting the recordings of simultaneous events by detectors located on nearly opposite sides of the ring.

A scintillator crystal comprising substantially pure lead carbonate ($PbCO_3$) has been found to possess a particularly favorable combination of stopping power, light yield and decay constant for use as a scintillator material in PET camera arrays such as that illustrated in FIG. 2. The relevant properties of $PbCO_3$ are compared to those of known scintillator materials in the following table.

TABLE I

|  | $PbCO_3$ | NaI(Tl) | $BaF_2$ | BGO |
|---|---|---|---|---|
| Decay Constant (nsec) | 8.5/34 | 250 | 0.6/620 | 300 |
| Light Yield | 2 | 100 | 16 | 8 |
| 1/tau (cm at 511 keV) | 1.2 | 3.0 | 2.3 | 1.1 |
| Hygroscopic | No | Very | Slightly | No |

As shown in Table I, substantially pure $PbCO_3$ provides a balance of stopping power, light yield and decay constant that is superior to other known scintillator materials. In particular, $PbCO_3$ exhibits a fast component having a decay constant of approximately 50% @8.5 nec, 50% @34 nec, both far superior to those of NaI(Tl) and BGO. With respect to light yield, $PbCO_3$ exhibits a value of 2 percent that of NaI(Tl); its light yield is thus about one-quarter that of BGO. In addition, the stopping power of $PbCO_3$ (1/tau=1.2 cm at 511 keV) is about the same as that of BGO. Finally, $PbCO_3$ exhibits no hygroscopy.

As shown in Table I, in contrast to NaI(Tl), $PbCO_3$ is superior in that its decay constant is far shorter than that of NaI(Tl) and it is not hygroscopic, making it much easier to handle than NaI(Tl).

As further shown in Table I, in contrast to $BaF_2$, $PbCO_3$ has superior stopping power (1/tau) but an inferior light yield. In addition, $PbCO_3$ has a fast component like $BaF_2$. While the decay constant of this fast component has not yet been precisely established, an upper limit of 10 nsec has been measured. Moreover, while the fast component of $BaF_2$ can only be detected using expensive quartz photomultiplier tubes, the fast component of $PbCO_3$ can be detected using less expensive glass photomultiplier tubes.

Finally, as shown in Table I, in contrast to BGO, $PbCO_3$ has a similar stopping power (1/tau), an inferior light yield, and a far superior decay constant. Thus, $PbCO_3$ provides adequate stopping power and light yield with an improved decay constant.

Figure 3:
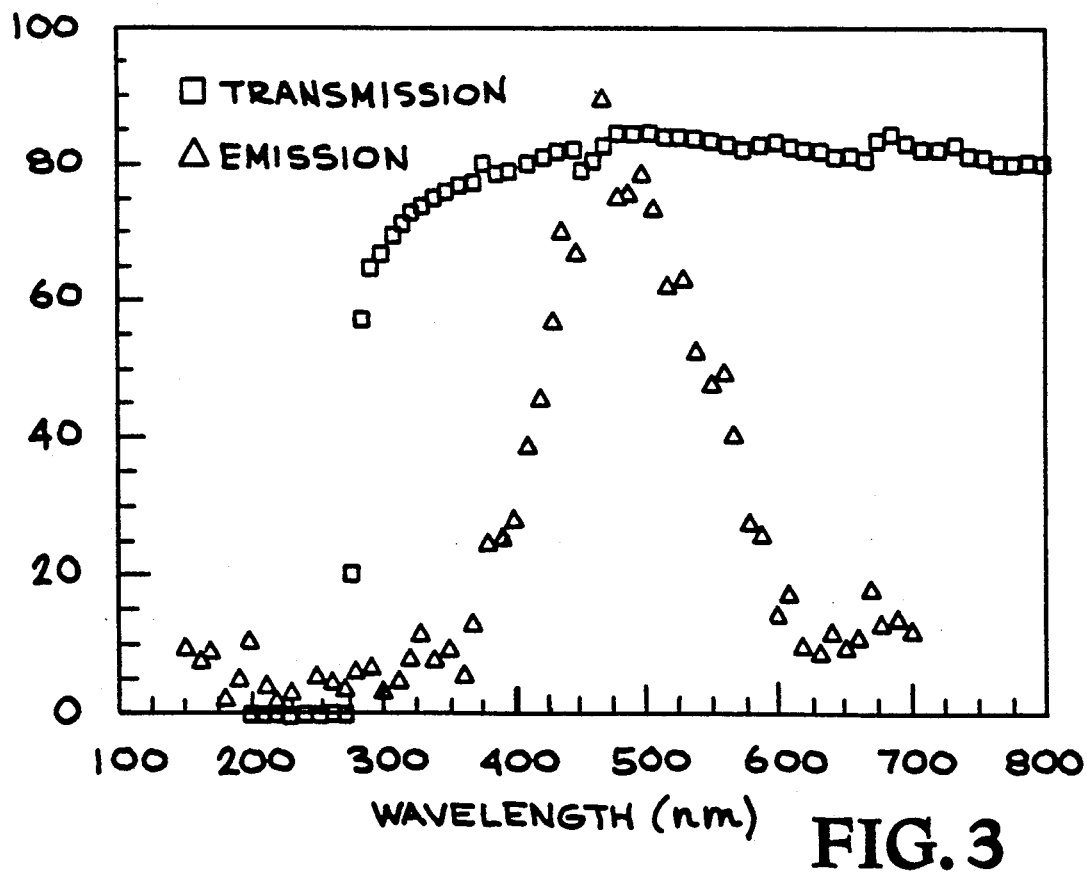
FIG. 3 is a graph showing the relative amount of light emitted (solid line) and transmitted (broken line) by wavelength from a lead carbonate scintillator crystal.

The emission and transmission spectra of substantially pure $PbCO_3$ are shown in FIG. 3. The emission spectrum of pure $PbCO_3$ shows emission in the wavelength range of about 375 nm to about 600 nm, with a peak at about 475 nm. With emission between 300 nm and 500 nm, most of the light can be detected efficiently by glass photomultiplier tubes. The transmission spectrum of pure $PbCO_3$ shows transmission in the wavelength range of about 280 nm and above, indicating that $PbCO_3$ is transparent to its own radiation.

Lead carbonate can be prepared in several crystalline forms. In British Patent No. 1,468,052, herein incorporated by reference, a process of preparing $PbCO_3$ is disclosed by introducing a fraction of lead hydroxide [$Pb(OH)_2$]. The exact fraction of lead hydroxide is arbitrary, and consequently the resulting crystal could contain lead hydroxide almost entirely and very little lead carbonate. If the ratio is $\frac{2}{3}$ lead carbonate and $\frac{1}{3}$ lead hydroxide, the compound is known as basic lead carbonate. However, the scintillation properties of lead carbonate are essentially unaltered by the presence of lead hydroxide and so the fraction of lead hydroxide contained in the resulting scintillation crystal is likely to be determined by manufacturing convenience rather than effectiveness as a scintillator.

In addition to the discovery that substantially pure $PbCO_3$ exhibits favorable scintillation properties, is to be appreciated that $PbCO_3$ doped with certain additives could provide improved scintillator materials. In general, such dopants can (1) effect a shift in the location of the wavelength peak of the emission spectrum, (2) reduce the decay time, or (3) increase the light yield of the material.

While particular embodiments and applications of the present invention have been shown, it will be understood, of course, that the invention is not limited thereto since modifications may be made by those skilled in the art, particularly in light of the foregoing teachings. It is therefore contemplated by the appended claims to cover any such modifications as incorporate those features which come within the true spirit and scope of the invention.

What is claimed is:

1. A radioisotope camera comprising:
   (a) a plurality of scintillator elements capable of converting gamma-radiation to optical radiation selected from the group of materials consisting essentially of lead carbonate and basic lead carbonate, each scintillator element being arranged in close proximity to each other and positioned to receive gamma radiation from a subject;
   (b) a plurality of photodetectors positioned to receive optical radiation directly from the scintillator elements and convert the optical radiation into electrical pulses; and
   (c) means connected to the photodetectors for responding to the electrical pulses generated by the photodetectors and reconstructing the spatial distribution of gamma radiation from the subject.

2. The radioisotope camera of claim 1 wherein each photodetector comprises a photomultiplier tube coupled to a scintillator element.

3. The radioisotope camera of claim 1 wherein each photodetector comprises a solid-state photodiode coupled to a scintillator element.

4. The radioisotope camera of claim 1 wherein each scintillator element contains a scintillation-enhancing dopant.

5. The radioisotope camera of claim 1 wherein the scintillation elements are in a circular array configuration and comprise means for detecting positron emission.

6. A method of measuring the position of gamma radiation from a subject comprising:
 (a) providing a radiation detector comprising (i) a plurality of scintillator elements capable of converting gamma radiation to optical radiation selected from the group of materials consisting essentially of lead carbonate and basic lead carbonate, each scintillator element being arranged in close proximity to each other and positioned to receive gamma radiation from a subject, (ii) a plurality of photodetectors positioned to receive optical radiation directly from the scintillator elements and convert it into electrical pulses, and (iii) means connected to the photodetectors for responding to the electrical pulses generated by the photodetectors and reconstructing spatial distribution of gamma radiation from the subject.
 (b) exposing the scintillator elements to radioactive emissions; and
 (c) reconstructing the spatial distribution of the radioactive emissions from the subject from the electrical pulses generated by the photodetectors.

7. The method of claim 6 wherein said gamma radiation is of high energy.

8. The method of claim 6 wherein the scintillator elements contain a scintillation-enhancing dopant.

9. The method of claim 6 wherein the scintillator elements of the radiation detector are in a circular array configuration and disposed about a radioactive emitting subject whereby the reconstructing step results in a positron emission tomograph.

* * * * *